(12) United States Patent
Dai et al.

(10) Patent No.: US 10,661,254 B2
(45) Date of Patent: May 26, 2020

(54) COMPOSITE CATALYST AND PREPARATION METHOD THEREFOR

(71) Applicants: China Petroleum & Chemical Corporation, Beijing (CN); Beijing Research Institute of Chemical Industry, China Petroleum & Chemical Corporation, Beijing (CN)

(72) Inventors: Wei Dai, Beijing (CN); Shuliang Lu, Beijing (CN); Haibin Jiang, Beijing (CN); Guoqing Wang, Beijing (CN); Xiaohong Zhang, Beijing (CN); Hui Peng, Beijing (CN); Jinliang Qiao, Beijing (CN)

(73) Assignees: China Petroleum & Chemical Corporation, Beijing (CN); Beijing Research Institute of Chemical Industry, China Petroleum & Chemical Corporation, Beijing (CN)

( * ) Notice: Subject to any disclaimer, the term of this patent is extended or adjusted under 35 U.S.C. 154(b) by 0 days.

(21) Appl. No.: 15/257,603

(22) Filed: Sep. 6, 2016

(65) Prior Publication Data
US 2016/0367972 A1 Dec. 22, 2016

Related U.S. Application Data

(63) Continuation of application No. PCT/CN2015/073783, filed on Mar. 6, 2015.

(30) Foreign Application Priority Data

Mar. 7, 2014 (CN) .......................... 2014 1 0083872

(51) Int. Cl.
| | | |
|---|---|---|
| *B01J 31/34* | (2006.01) | |
| *C01B 3/58* | (2006.01) | |
| *B01J 25/02* | (2006.01) | |
| *B01J 21/18* | (2006.01) | |
| *C07C 29/141* | (2006.01) | |
| *C07C 1/04* | (2006.01) | |
| *C07C 5/08* | (2006.01) | |
| *B01J 37/02* | (2006.01) | |
| *C07C 209/36* | (2006.01) | |
| *C07C 5/03* | (2006.01) | |
| *B01J 37/04* | (2006.01) | |
| *B01J 37/08* | (2006.01) | |

(52) U.S. Cl.
CPC .............. *B01J 25/02* (2013.01); *B01J 21/18* (2013.01); *B01J 37/0201* (2013.01); *B01J 37/04* (2013.01); *B01J 37/084* (2013.01); *C07C 1/0435* (2013.01); *C07C 1/0445* (2013.01); *C07C 5/03* (2013.01); *C07C 5/08* (2013.01); *C07C 29/141* (2013.01); *C07C 209/36* (2013.01); *C07C 2521/04* (2013.01); *C07C 2521/06* (2013.01); *C07C 2521/18* (2013.01); *C07C 2523/26* (2013.01); *C07C 2523/28* (2013.01); *C07C 2523/44* (2013.01); *C07C 2523/46* (2013.01); *C07C 2525/00* (2013.01); *C07C 2525/02* (2013.01)

(58) Field of Classification Search
None
See application file for complete search history.

(56) References Cited

U.S. PATENT DOCUMENTS

| | | | |
|---|---|---|---|
| 2,928,891 | A | 3/1960 | Eduard et al. |
| 3,617,389 | A | 11/1971 | Kuhn et al. |
| 4,826,799 | A | 5/1989 | Cheng et al. |
| 5,488,023 | A | 1/1996 | Gadkaree et al. |
| 5,733,838 | A | 3/1998 | Vicari et al. |
| 6,136,749 | A | 10/2000 | Gadkaree et al. |
| 2003/0019794 | A1 | 1/2003 | Schmidt et al. |
| 2010/0094058 | A1 | 4/2010 | Lettermann et al. |
| 2012/0231338 | A1 | 9/2012 | Matsuzaka et al. |
| 2015/0231612 | A1 | 8/2015 | Dai et al. |
| 2016/0367972 | A1 | 12/2016 | Dai et al. |

FOREIGN PATENT DOCUMENTS

| | | |
|---|---|---|
| CN | 1212903 A | 4/1999 |
| CN | 1877886 A | 12/2006 |
| CN | 102648050 A | 8/2012 |
| CN | 103566976 A | 2/2014 |
| CN | 103566979 A | 2/2014 |
| CN | 104888808 A | 9/2015 |
| CN | 104945227 A | 9/2015 |
| CN | 105399605 A | 3/2016 |
| EP | 1371607 A2 | 12/2003 |
| JP | S5964511 A | 4/1984 |
| JP | 2000140643 A | 5/2000 |
| JP | 2009173505 A | 8/2009 |
| RU | 2170140 C2 | 7/2001 |
| RU | 2174047 C2 | 9/2001 |

OTHER PUBLICATIONS

International Search Report dated Jun. 15, 2015 for International Application No. PCT/CN2015/073783, filed Mar. 6, 2015.
Written Opinion of the International Searching Authority dated Jun. 15, 2015 for International Application No. PCT/CN2015/073783, filed Mar. 6, 2015.
International Preliminary Report on Patentability dated Sep. 13, 2016 for International Application No. PCT/CN2015/073783, filed Mar. 6, 2015.
Office Action issued in connection with corresponding Japanese Patent Application No. 2016-572882 dated Jan. 8, 2019, 4 pages.
Extended European Search Report for European Patent Application No. EP15758855.9 dated Apr. 19, 2018.

*Primary Examiner* — Yun Qian
(74) *Attorney, Agent, or Firm* — Duane Morris LLP

(57) ABSTRACT

Disclosed is a composite catalyst, comprising carbon in a continuous phase and Raney alloy particles in a dispersed phase. The Raney alloy particles are dispersed evenly or unevenly in the carbon in a continuous phase, and the carbon in a continuous phase is obtained by carbonizing at least one carbonizable organic substance. The catalyst has good particle strength, high catalytic activity, and good selectivity.

18 Claims, 1 Drawing Sheet

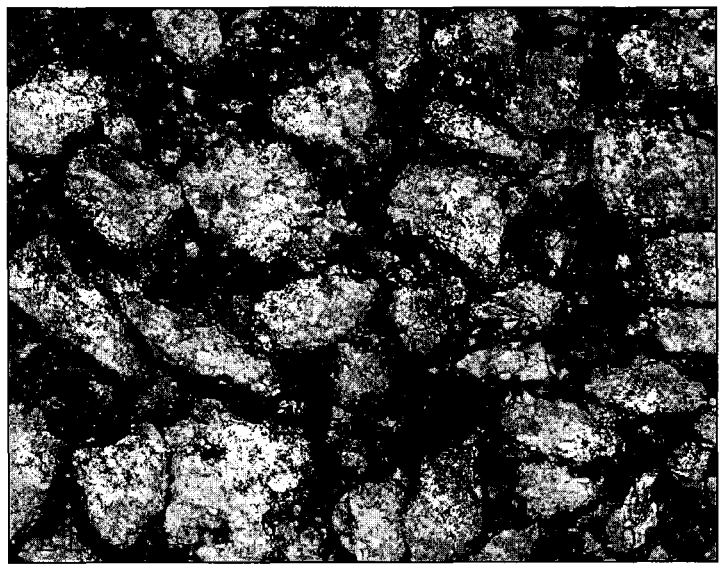

COMPOSITE CATALYST AND PREPARATION METHOD THEREFOR

CROSS REFERENCE TO RELATED APPLICATIONS

The present application is a continuation application of PCT application No. PCT/CN2015/073783, filed on Mar. 6, 2015, which claims the benefit of the Chinese Patent Application No. 201410083872.9, filed on Mar. 7, 2014, the teachings of which are incorporated herein by reference in their entirety and for all purposes.

FIELD OF THE INVENTION

The present invention relates to a composite catalyst and a method for the preparation thereof, and specifically to a catalyst, in which Raney alloy particles are dispersed as a dispersed phase in a continuous phase, and a method for the preparation thereof.

BACKGROUND ART

In the catalysis field, "Raney method" is one of methods for preparing an active metal catalyst, and such a method comprises: i) preparing a two- or more-component alloy containing an active metal at first, and ii) leaching out at least one metal component, leaving a metal having a high catalytic activity and a porous structure. Step ii) is also referred to as "activation". For example, M. Raney invents at the earliest a Raney nickel catalyst (Industrial and Engineering Chemistry, 1940, Vol. 32, 1199), which catalyst is prepared as follows: a nickel-aluminum alloy is prepared at first, the aluminum element in the alloy is then dissolved with a strong base solution, leaving nickel metal having a porous structure and a very high catalytic activity.

Raney catalysts include Raney nickel catalysts, Raney cobalt catalysts, Raney copper catalysts and the like, among which Raney nickel catalysts are the most common. Raney nickel catalysts are usually in the form of powder and flammable so that their handling is inconvenient. Thus, Raney nickel catalysts are mostly used in small-scale catalytic hydrogenation reaction in the fine chemical field, but cannot be used in a conventional fixed bed reaction.

In order to expand the application field of the Raney nickel catalysts, forming them into a shape by a certain method, especially into a fixed bed catalyst, is a research direction drawing many attentions in recent years.

Patent application CN1557918 discloses a shaped Raney nickel catalyst and its preparation, with the catalyst being prepared by directly kneading an alloy powder consisting of Al and one or more of Ni, Co, Cu and Fe, an inorganic matter such as pseudoboehmite as a binder, and a natural or synthetic organic matter such as Sesbania cannabina powder or carboxymethyl cellulose as a pore template agent, molding, calcining, and activating with a caustic solution. The catalyst has a certain shape and strength, and may be used as a fixed bed catalyst.

U.S. Pat. No. 5,536,694 discloses a shaped, activated Raney metal fixed bed catalyst, which is obtained by molding at least one catalyst alloy powder, a pure Raney method metal powder as a binder, a shaping aid, and a pore-producer, followed by calcination and activation with a caustic solution.

U.S. Pat. No. 4,826,799 discloses a method for preparing a shaped Raney catalyst, comprising sufficiently uniformly mixing a Raney alloy with a polymer, a mineral oil, etc. at a certain temperature, shaping the resultant mixture by a method such as extrusion, then burning off the polymer or remaining the polymer, and finally leaching out metallic aluminum with a strong base solution to afford an activated catalyst. This method can easily afford a shaped catalyst. However, if the polymer is remained, then due to the wrapping or covering of the Raney alloy by the polymer during the shaping, there are less catalytically active sites so that the catalyst has a relatively low or even no catalytic activity; if the polymer is burned off by a high-temperature calcination, then quite a number of particles will be sintered so that the activity is low.

Therefore, there is still a need to a Raney catalyst which has a high activity, a good selectivity and a good particle strength and can be used in fixed beds.

SUMMARY

An objective of the present invention is to provide a composite catalyst comprising carbon as a continuous phase and Raney alloy particles as a dispersed phase, wherein the Raney alloy particles are uniformly or non-uniformly dispersed in the carbon continuous phase, and wherein the carbon as a continuous phase is obtained by carbonizing at least one carbonizable organic matter. The catalyst has the following advantages: its preparation method is simple, catalyst product has fewer impurities, the loading amount of the active metal is high, the strength of catalyst particles is good, and when used in a hydrogenation reaction, the catalyst has a high activity and a good selectivity.

A further objective of the present invention is to provide a method for preparing the catalyst, comprising the steps of
a) formulating a solidifiable composition, wherein the solidifiable composition or a solidified product thereof comprises a carbonizable organic matter, and the solidifiable composition may be in the form of liquid, glue, paste or powder;
b) mixing Raney alloy particles with the solidifiable composition from step a), then solidifying the resultant mixture, and optionally crushing the solidified mixture, to obtain a catalyst precursor; and
c) under inert atmosphere, high-temperature carbonizing the catalyst precursor from step b), to afford the composite catalyst.

A still further objective of the present invention is to provide a method for the activation of the composite catalyst, comprising treating the composite catalyst with a caustic aqueous solution.

A still further objective of the present invention is to provide an activated catalyst comprising carbonized organic matter as a carrier and activated Raney alloy particles. The activated catalyst is obtained by the above-described activation method.

A still further objective of the present invention is to provide use of the activated catalyst in hydrogenation, dehydrogenation, amination, dehalogenation or desulfuration reactions.

BRIEF DESCRIPTION OF DRAWINGS

FIG. 1 is a scanning electron micrograph of the catalyst particles after carbonization prepared in Example 6.

DETAILED DESCRIPTION OF PREFERRED EMBODIMENTS

In a first aspect, the present invention relates to a composite catalyst comprising carbon as a continuous phase and Raney alloy particles as a dispersed phase, wherein the Raney alloy particles are uniformly or non-uniformly dispersed in the carbon continuous phase, and wherein the carbon as a continuous phase is obtained by carbonizing at least one carbonizable organic matter.

In an embodiment, the Raney alloy comprises at least one Raney metal and at least one leachable element. As used herein, the term "Raney metal" is intended to mean a catalytically active metal which is insoluble when activated by Raney method. Examples of Raney metal include, but are not limited to, nickel, cobalt, copper and iron. As used herein, the term "leachable element" is intended to mean a soluble element when activated by Raney method. Examples of leachable element include, but are not limited to, aluminum, zinc and silicon.

In a preferred embodiment, the Raney alloy is selected from the group consisting of nickel-aluminum alloy, cobalt-aluminum alloy and copper-aluminum alloy.

In an embodiment, the weight ratio of the Raney metal to the leachable element in the Raney alloy ranges from 1:99 to 10:1, preferably from 1:10 to 4:1, more preferably from 1:3 to 2:1, and most preferably about 1:1.

The particle size of the Raney alloy particles may be selected in a broad range. For example, the average particle size may range from 0.1 to 1000 microns, preferably from 1 to 500 microns, and more preferably from 10 to 100 microns.

In an embodiment, in order to enhance activity or selectivity of the catalyst, it is also possible to introduce at least one promoter into the Raney alloy, to form a multiple-component Raney alloy. The at least one promoter may be selected from the group consisting of Mo, Cr, Ti, Pt, Pd, Rh and Ru. The amount of the promoter may range from 0.01 wt % to 5 wt %, based on the total weight of the Raney alloy.

As used herein, the term "carbonizable organic matter" is intended to mean an organic matter, which may be converted into a synthetic material having a high carbon content (for example, at least 80 wt %) through a treatment conducted at a certain temperature under oxygen-poor or oxygen-free atmosphere so as to volatilize all or most of non-carbonaceous elements therein such as hydrogen, oxygen, nitrogen, sulfur, or the like. The resulting carbon-containing synthetic material has properties of high-temperature resistance, high strength, high modulus, being porous.

In an embodiment, the carbonizable organic matter is preferably an organic polymer, including natural organic polymer and synthetic organic polymer. Examples of natural organic polymer include, but are not limited to, starches, modified starches, celluloses, carboxymethylcelluloses and lignins. Examples of the synthetic organic polymer include, but are not limited to, plastics including thermosetting plastics and thermoplastic plastics, and rubbers. In a preferred embodiment, the carbonizable organic matter is a thermosetting plastic.

In an embodiment, the carbonizable organic matter is at least one selected from the group consisting of epoxy resins, phenolic resins, furan resins, polystyrenes, poly(styrene-co-divinylstyrene)s, polyacrylonitriles, starches, modified starches, viscose fiber, lignins, celluloses, carboxymethylcelluloses, butadiene-styrene rubbers, polyurethane rubbers.

In other embodiments, the carbonizable organic matter is selected from the group consisting of coal, natural bitumen, asphalt and coal-tar pitch.

According to the present invention, the carbonizable organic matter is mixed with the Raney alloy particles, then the resultant mixture is subjected to carbonization treatment to form a composite of carbon and Raney alloy particles, i.e., the composite catalyst according to the present invention. Without limited by any specific theory, it is believed that the Raney alloy promotes the carbonization of the mixture so that the carbonization is carried out more completely. After the carbonization, the Raney alloy particles are dispersed in and firmly bonded to a porous carbon continuous phase so that the composite catalyst has a very high strength. At the same time, since the Raney alloy particles are dispersed in the porous carbon continuous phase, they are accessible to a solution. Thus, when the composite catalyst is activated with an alkali solution, the Raney alloy particles can be easily activated to form a porous high-activity Raney metal. Moreover, it is believed that a small amount of amorphous carbon in the composite catalyst is also washed off during the activation so that the carbon continuous phase material is hole-enlarged and therefore more Raney alloy particles are exposed. As a result, the composite catalyst according to the present invention contains little or no Raney alloy particles inaccessible to an alkali solution so that the activated catalyst has a very high catalytic activity.

The content of the Raney alloy in the composite catalyst according to the present invention may vary widely, but preferably ranges from 10 to 90 wt %, and preferably from 40 to 80 wt %, based on the total weight of the composite catalyst.

There is no specific limitation to the shape of the composite catalyst according to the present invention, as long as it is suitable for fixed bed processes or fluidized bed processes, especially for fixed bed processes. Conveniently, the composite catalyst may be in the form of sphere, semisphere, ring, semi-ring, trilobal extrudate, cylinder, semi-cylinder, hollow cylinder, prism, cube, cuboid, tablet, pellet, irregular particles, and the like.

The particle size of the composite catalyst according to the present invention may vary widely, depending on the preparation method and the intended use of the catalyst. The average equivalent diameter of the composite catalyst particles typically ranges from 0.3 mm to 20 mm, preferably from 0.5 mm to 10 mm, and more preferably from 1 mm to 8 mm.

In a second aspect, the present invention further provides a method for preparing the above-described composite catalyst, comprising the steps of:

a) formulating a solidifiable composition, wherein the solidifiable composition or a solidified product thereof comprises a carbonizable organic matter, and the solidifiable composition may be in the form of liquid, glue, paste or powder;

b) mixing Raney alloy particles with the solidifiable composition from step a), then solidifying the resultant mixture, and optionally crushing the solidified mixture, to obtain a catalyst precursor; and c) under inert atmosphere, high-temperature carbonizing the catalyst precursor from step b), to afford the composite catalyst.

In the method of the present invention, the Raney alloy particles and the carbonizable organic matter are as described for the first aspect.

The composition of the solidifiable composition is generally depended on the selected carbonizable organic matter. In some embodiments, when the selected carbonizable organic matter is a thermoplastic plastic, the solidifiable composition may consist essentially of the powder of the thermoplastic plastic. Such a solidifiable composition may be solidified by heating and cooling.

In some other embodiments, the solidifiable composition may comprise carbonizable organic matter and a solvent and/or a liquid dispersant. Such a solidifiable composition may be solidified by removing at least part of the solvent and/or liquid dispersant. Examples of the solvent and liquid dispersant include, but are not limited to, water; C1 to C8 alcohols such as methanol, ethanol, isopropanol, n-butanol, 2-ethylhexanol; esters such as ethyl acetate, methyl acetate; ketones such as acetone, methyl ethyl ketone, cyclohexone; C5 to C30 hydrocarbons, such as pentane, cyclopentane, hexane, cyclohexane, heptane, octane, decane, dodecane, benzene, toluene, xylene; C1 to C10 halo-hydrocarbons. In such a solidifiable composition, the lower limit of the concentration of the carbonizable organic matter may be 5, 10, 15, 20, 25, 30, 35 or 40 wt %, and the upper limit may be 20, 30, 40, 45, 50, 55, 60, 65, 70, 75, 80, 85, 90 or 95 wt %.

In some other embodiments, the solidifiable composition may comprises a thermosetting resin and, if desired, a curing agent. Such a solidifiable composition may be solidified by heating. The curing systems suitable for the curing of various thermosetting resins are well-known by those skilled in the art.

When formulating the solidifiable composition, one or more additives selected from the group consisting of binders, cure accelerators, dyes, pigments, colorants, antioxidants, stabilizers, plastizers, lubricants, flow modifiers or aids, flame retardants, anti-sag agents, anti-blocking agents, adhesion promoters, conductive additives, multi-valent metal ions, impact modifiers, release agents, nucleating agent and the like may be optionally added. The amounts of these additives may be those conventionally employed or may be adjusted according to actual demand.

The formulated solidifiable composition may be in the form of liquid state system, liquid-solid system, glue-like system, or powdery solid system.

In some specific embodiments, the method for preparing the composite catalyst according to the present invention comprises the steps of:

a) formulating a solidifiable system according to a conventional solidification regime of the carbonizable organic matter, wherein the solidifiable system may be in the form of liquid or powder;

b) uniformly mixing the Raney alloy particles with the solidifiable system, then performing mold compression solidification, and optionally crushing the solidified mixture, to obtain a catalyst precursor; and c) under inert atmosphere, high-temperature carbonizing the catalyst precursor from step b), to afford the composite catalyst.

In the present method, the Raney alloy particles and the carbonizable organic matter are as described for the first aspect.

In step b), the weight ratio of the Raney alloy particles to the solidifiable composition ranges from 1:99 to 99:1, preferably from 10:90 to 90:10, more preferably from 25:75 to 75:25, and even more preferably from 40:60 to 60:40.

In step b), the catalyst precursor is obtained by solidifying the mixture of the Raney alloy particles and the solidifiable composition and optionally crushing the solidified mixture. The manner and process conditions of the solidification are depended on the composition of the solidifiable composition, and may be easily determined by those skilled in the art. For example, if a thermoplastic resin is used as the carbonizable organic matter in the solidifiable composition, then the solidification of the solidifiable composition may be accomplished by heating the mixture of the Raney alloy particles and the solidifiable composition to a temperature above the softening temperature of the thermoplastic resin and then cooling; if a thermosetting resin is used as the carbonizable organic matter in the solidifiable composition, then the solidification of the solidifiable composition may be accomplished by heating the mixture of the Raney alloy particles and the solidifiable composition to initiate a curing reaction; if a natural organic polymer such as a starch, a modified starch, a cellulose, a carboxymethylcellulose or a lignin is used as the carbonizable organic matter in the solidifiable composition, then the solidification of the solidifiable composition may be accomplished by removing a liquid medium in the mixture of the Raney alloy particles and the solidifiable composition and/or heating the mixture of the Raney alloy particles and the solidifiable composition. If desired, the solidified mixture obtained through the solidification operation may be processed into particles with a desired shape and a desired size by using any of the methods known in the art such as cutting, tailoring, punching and breaking.

The particle size and shape of the catalyst precursor are substantially the same as those described in the first aspect for the composite catalyst.

In step c), the carbonification is typically carried out in a tubular furnace. The carbonification temperature typically ranges from 400 to 1900° C., and preferably from 600 to 950° C., protective gas is an inert gas such as nitrogen or argon, and the carbonification is carried out for 1 to 12 hours. For example, a phenolic resin may be completely carbonized through carbonizing at 850° C. for 3 hours, to form porous carbon. A higher carbonizing temperature may render the carbon obtained by the carbonizing more regular.

The composite catalyst according to the present invention may be easily activated. This constitutes a third aspect of the present invention.

Methods for activating the composite catalyst and conditions employed therein are known per se. For example, the composite catalyst may be activated by treating it with a caustic aqueous solution having a concentration of from 0.5 to 50 wt %, preferably from 1 to 40 wt %, and more preferably from 5 to 30 wt % at a temperature of from 25° C. to 95° C. for about 5 minutes to 72 hours, to leach out at least a portion of the leachable element, for example, at least one of aluminum, zinc, and silicon, present in the Raney alloy. In an embodiment, the caustic aqueous solution is a sodium hydroxide aqueous solution or a potassium hydroxide aqueous solution.

In a fourth aspect, the present invention relates to an activated Raney catalyst prepared by the above-described activation method. The activated Raney catalyst comprises carbonized organic matter as a carrier and activated Raney alloy particles. According to the present invention, by controlling the loading amount of Raney alloy particles in the preparation of the catalyst and/or controlling the activation degree of the catalyst, the loading amount of the Raney metal in the activated catalyst may be readily controlled. In an embodiment, the loading amount of the Raney metal in the activated catalyst according to the invention ranges from 1 to 90 wt %, preferably 10 to 90 wt %, and more preferably from 40 to 80 wt %, based on the total weight of the activated catalyst.

The activated catalyst of the invention has a good strength and can be used for fixed bed or fluidized bed catalytic reactions.

The activated catalyst of the invention may be used for hydrogenation, dehydrogenation, amination, dehalogenation, desulfuration, and the like, preferably for hydrogenation, such as olefin hydrogenation, alkyne hydrogenation, arene hydrogenation, carbonyl hydrogenation, nitro hydrogenation, nitrile hydrogenation, and more preferably for hydrogenation of aldehyde to alcohol, hydrogenation of CO, hydrogenation of benzene, or hydrogenation of nitrobenzene to aniline.

Therefore, in a fifth aspect, the present invention provides use of the activated catalyst of the invention in hydrogenation, dehydrogenation, amination, dehalogenation, or desulfuration.

In some embodiments, the present invention relates to a process of converting an organic compound, which process comprises contacting the organic compound feedstock with the activated catalyst of the invention under suitable conversion conditions, and recovering converted organic compound.

In a particular embodiment, the present invention relates to a process for hydrogenating an organic compound, which process comprises contacting the organic compound feedstock with the activated catalyst of the invention in the presence of hydrogen under suitable hydrogenation conditions, and recovering hydrogenated organic compound.

In an embodiment, the conversion process or the hydrogenation process is a fixed bed or fluidized bed process.

The process conditions of the conversion process are well known by those skilled in the art.

The present catalysts are shaped catalysts, have good particle strength and very high activity, and can be used for fixed bed, removing bed or fluidized bed reactions.

The method for preparing the present catalysts is simple and low in cost.

EXAMPLES

The following examples are given for further illustrating the invention, but do not make limitations to the invention in any way.

Example 1

(1) A curable epoxy resin system was prepared by stirring uniformly 100 parts by mass of liquid epoxy resin (CYD-128, available from Baling Petrochemical Co.), 85 parts by mass of methyl tetrahydrophthalic anhydride (MeTHPA) (available from Shengshida Technology and Trade Co., Ltd., Guangdong) as a curing agent, and 1.5 parts by mass of triethanolamine (TEA) (available from Tianjin Chemical Reagent First Factory) as a curing accelerator.

(2) 40 g of the formulated epoxy resin system from step (1) were weighted and mixed by adequately stirring with 180 g of 100 mesh to 200 mesh powdery nickel-aluminum alloy having a Ni content of 48 wt % and an aluminum content of 52 wt %. A proper amount of the resulting mixture was added into a mould having Φ5 mm cylindrical pores, and the mould was then placed in a platen press and then mould pressed at a temperature of 120° C. under a pressure of 7 MPa for 30 minutes and then at a temperature of 150° C. under a pressure of 7 MPa for 90 minutes. After cooling, the solidified product was removed to obtain a particulate catalyst precursor.

(3) 100 ml of the catalyst precursor was placed in a tubular high-temperature electric furnace. Under a nitrogen flow rate of 200 ml/min, the temperature was raised at a rate of 10° C./min to 600° C. and maintained for 3 hours. After cooling, a composite catalyst was obtained.

(4) 400 g of 20% aqueous NaOH solution was formulated by using deionized water and added to 50 ml of the catalyst from step (3). The resulting mixture was maintained at 85° C. for 4 hours, then the liquid was filtered off, and the solids were washed with deionized water to near neutrality, to afford an activated composite catalyst. The activated catalyst was reserved in deionized water for use. The activated catalyst was found to have a nickel content of 60 wt %, based on the weight of the activated catalyst.

Example 2

(1) A curable epoxy resin system was prepared by stirring uniformly 100 parts by mass of liquid epoxy resin (CYD-128, available from Baling Petrochemical Co.), 85 parts by mass of methyl tetrahydrophthalic anhydride (MeTHPA) (available from Shengshida Technology and Trade Co., Ltd., Guangdong) as a curing agent, and 1.5 parts by mass of triethanolamine (TEA) (available from Tianjin Chemical Reagent First Factory) as a curing accelerator.

(2) 50 g of the formulated curable epoxy resin system from step (1) were weighted and mixed by adequately stirring with 150 g of 100 mesh to 200 mesh powdery nickel-aluminum alloy having a Ni content of 48 wt % and an aluminum content of 52 wt %. A proper amount of the resulting mixture was added into a mould having Φ5 mm cylindrical pores, and the mould was then placed in a platen press and then mould pressed at a temperature of 120° C. under a pressure of 7 MPa for 30 minutes and then at a temperature of 150° C. under a pressure of 7 MPa for 90 minutes. After cooling, the solidified product was removed to obtain a particulate catalyst precursor.

(3) 100 ml of the catalyst precursor was placed in a tubular high-temperature electric furnace. Under a nitrogen flow rate of 200 ml/min, the temperature was raised at a rate of 10° C./min to 700° C. and maintained for 3 hours. After cooling, a composite catalyst was obtained.

(4) 400 g of 20% aqueous NaOH solution was formulated by using deionized water and added to 50 ml of the catalyst from step (3). The resulting mixture was maintained at 85° C. for 4 hours, then the liquid was filtered off, and the solids were washed with deionized water to near neutrality, to afford an activated composite catalyst. The activated catalyst was reserved in deionized water for use. The activated catalyst was found to have a nickel content of 50 wt %, based on the weight of the activated catalyst.

Example 3

(1) A curable epoxy resin system was prepared by stirring uniformly 100 parts by mass of liquid epoxy resin (CYD-128, available from Baling Petrochemical Co.), 85 parts by mass of methyl tetrahydrophthalic anhydride (MeTHPA) (available from Shengshida Technology and Trade Co., Ltd., Guangdong) as a curing agent, and 1.5 parts by mass of triethanolamine (TEA) (available from Tianjin Chemical Reagent First Factory) as a curing accelerator.

(2) 50 g of the formulated curable epoxy resin system from step (1) were weighted and mixed by adequately stirring with 130 g of 100 mesh to 200 mesh powdery nickel-aluminum alloy having a Ni content of 48 wt % and an aluminum content of 52 wt %. A proper amount of the resulting mixture was added into a mould having Φ5 mm cylindrical pores, and the mould was then placed in a platen press and then mould pressed at a temperature of 120° C. under a pressure of 7 MPa for 30 minutes and then at a temperature of 150° C. under a pressure of 7 MPa for 90 minutes. After cooling, the solidified product was removed to obtain a particulate catalyst precursor.

(3) 100 ml of the catalyst precursor was placed in a tubular high-temperature electric furnace. Under a nitrogen flow rate of 200 ml/min, the temperature was raised at a rate of 10° C./min to 800° C. and maintained for 3 hours. After cooling, a composite catalyst was obtained.

(4) 400 g of 20% aqueous NaOH solution was formulated by using deionized water and added to 50 ml of the catalyst from step (3). The resulting mixture was maintained at 85° C. for 4 hours, then the liquid was filtered off, and the solids were washed with deionized water to near neutrality, to afford an activated composite catalyst. The activated catalyst was reserved in deionized water for use. The activated catalyst was found to have a nickel content of 45 wt %, based on the weight of the activated catalyst.

Example 4

(1) A curable epoxy resin system was prepared by stirring uniformly 100 parts by mass of liquid epoxy resin (CYD-128, available from Baling Petrochemical Co.), 85 parts by mass of methyl tetrahydrophthalic anhydride (MeTHPA) (available from Shengshida Technology and Trade Co., Ltd., Guangdong) as a curing agent, and 1.5 parts by mass of triethanolamine (TEA) (available from Tianjin Chemical Reagent First Factory) as a curing accelerator.

(2) 50 g of the formulated curable epoxy resin system from step (1) were weighted and mixed by adequately stirring with 110 g of 100 mesh to 200 mesh powdery nickel-aluminum alloy having a Ni content of 48 wt % and an aluminum content of 52 wt %. A proper amount of the resulting mixture was added into a mould having Φ5 mm cylindrical pores, and the mould was then placed in a platen press and then mould pressed at a temperature of 120° C. under a pressure of 7 MPa for 30 minutes and then at a temperature of 150° C. under a pressure of 7 MPa for 90 minutes. After cooling, the solidified product was removed to obtain a particulate catalyst precursor.

(3) 100 ml of the catalyst precursor was placed in a tubular high-temperature electric furnace. Under a nitrogen flow rate of 200 ml/min, the temperature was raised at a rate of 10° C./min to 600° C. and maintained for 3 hours. After cooling, a composite catalyst was obtained.

(4) 400 g of 20% aqueous NaOH solution was formulated by using deionized water and added to 50 ml of the catalyst from step (3). The resulting mixture was maintained at 85° C. for 4 hours, then the liquid was filtered off, and the solids were washed with deionized water to near neutrality, to afford an activated composite catalyst. The activated catalyst was reserved in deionized water for use. The activated catalyst was found to have a nickel content of 40 wt %, based on the weight of the activated catalyst.

Example 5

(1) A powdery phenolic resin and hexamethylene-tetramine as a curing agent at a weight ratio of hexamethylene-tetramine to phenolic resin of 12/100 were adequately mixed by using a high speed mixer. 100 g of the resulting mixture were adequately mixed by using a high speed mixer with 300 g of 100 mesh to 200 mesh powdery nickel-aluminum alloy having a Ni content of 48 wt % and an aluminum content of 52 wt %.

(2) The material from step (1) was charged into a mould and then mould pressed in a sheeting machine heated to 90° C., to afford a sheet of 2 mm thickness. The sheet was allowed to further cure in the sheeting machine at 150° C. under a pressure of 5 MPa for 10 min. The cured sheet of 2 mm thickness was mechanically cut to particles having a particle size of approximately 3 mm to 5 mm.

(3) 100 ml of the particles were placed in a tubular high-temperature electric furnace. Under a nitrogen flow rate of 200 ml/min, the temperature was raised at a rate of 10° C./min to 650° C. and maintained for 3 hours. After cooling, a composite catalyst was obtained.

(4) 400 g of 20% aqueous NaOH solution was formulated by using deionized water and added to 50 ml of the catalyst from step (3). The resulting mixture was maintained at 85° C. for 4 hours, then the liquid was filtered off, and the solids were washed with deionized water to near neutrality, to afford an activated composite catalyst. The activated catalyst was reserved in deionized water for use. The activated catalyst was found to have a nickel content of 40 wt %, based on the weight of the activated catalyst.

Example 6

(1) A powdery phenolic resin and hexamethylene-tetramine as a curing agent at a weight ratio of hexamethylene-tetramine to phenolic resin of 12/100 were adequately mixed by using a high speed mixer. 100 g of the resulting mixture were adequately mixed by using a high speed mixer with 350 g of 100 mesh to 200 mesh powdery nickel-aluminum alloy having a Ni content of 48 wt % and an aluminum content of 52 wt %.

(2) The material from step (1) was charged into a mould and then mould pressed in a sheeting machine heated to 90° C., to afford a sheet of 2mm thickness. The sheet was allowed to further cure in the sheeting machine at 150° C. under a pressure of 5MPa for 10 min. The cured sheet of 2 mm thickness was mechanically cut to particles having a particle size of approximately 3 mm to 5 mm.

(3) 100 ml of the particles were placed in a tubular high-temperature electric furnace. Under a nitrogen flow rate of 200 ml/min, the temperature was raised at a rate of 10° C./min to 600° C. and maintained for 3 hours. After cooling, a composite catalyst was obtained.

(4) 400 g of 20% aqueous NaOH solution was formulated by using deionized water and added to 50 ml of the catalyst from step (3). The resulting mixture was maintained at 85° C. for 4 hours, then the liquid was filtered off, and the solids were washed with deionized water to near neutrality, to afford an activated composite catalyst. The activated catalyst was reserved in deionized water for use. The activated catalyst was found to have a nickel content of 45 wt %, based on the weight of the activated catalyst.

Comparative Example 1

Alumina-supported nickel-based low-temperature methanation catalyst:

An alumina-supported nickel-based catalyst was prepared by impregnation method according to Example 1 of patent CN100490972 C. The catalyst contains 40wt % nickel and can be used in the low-temperature methanation to remove a minor amount of CO in hydrogen gas.

Comparative Example 2

Alumina-supported nickel-based catalyst for the hydrogenation of aldehydes:

291 Grams of $Ni(NO_3)_2 \cdot 6H_2O$ were dissolved in 150g of deionized water, and 103 g of pseudoboehmite were added thereto. Next, 5% NaOH solution was added dropwise with stirring until the nickel was completely precipitated. A mixture of the pseudoboehmite and nickel hydroxide was filtered out and washed to near neutrality, oven dried at 120°

C., calcined at 500° C., and then tableted, to afford an alumina supported nickel-based catalyst. After having been reduced with hydrogen gas at 450° C., said catalyst contains 45 wt % of nickel and can be used in the hydrogenation of an aldehyde to an alcohol.

Comparative Example 3

Fixed bed Raney nickel catalyst containing alumina as a binder:

A catalyst was prepared by following the method described in patent CN1557918, said method using pseudoboehmite as a binder and comprising the steps of adding Sesbania cannabina powder, diluted nitric acid, etc., blending, extruding, cutting to form small cylindrical particles sizing Φ3 mm×3 mm, baking, calcining at 900° C., activating through base washing, washing with deionized water to near neutrality, and reserving in deionized water for use, with the final catalyst having a Ni content of 50 wt %.

Comparative Example 4

10 g of polypropylene powder and 100 g of nickel-aluminum alloy powder having a Ni content of 48 wt % and an Al content of 52 wt % were blended in a high speed mixer and then extruded from a twin-screw extruder at an extrusion temperature of 200° C. The extrudates were cut into small cylindrical particles sizing Φ3 mm×3 mm.

400 g of 20% aqueous NaOH solution was formulated by using deionized water and added to 40 g of the above-prepared nickel-aluminum alloy-polypropylene cylindrical particles. The resulting mixture was maintained at 85° C. for 8 hours, then the liquid was filtered off, and the solids were washed with deionized water to near neutrality, to afford an activated catalyst. The activated catalyst was reserved in deionized water for use. The activated catalyst was found to have a nickel content of 45 wt %, based on the weight of the activated catalyst.

Example 7

Performance test in CO methanation reaction:

6 ml of catalyst were charged into a stainless steel fixed bed reactor, and then highly pure nitrogen gas was passed through the reactor at a flow rate of 300 ml/min. The reactor was heated to 120° C. and maintained at that temperature for 2 hours. Then, the highly pure nitrogen gas was switched to hydrogen gas at a flow rate of 300 ml/min, and the reactor was heated to 150° C. Next, the feed gas was switched to a crude hydrogen feedstock containing 5800 ppm CO to start the reaction, with the reaction pressure being 2.8 MPa and the reaction temperature being controlled at 170° C. The flow rate of the crude hydrogen feedstock was altered to obtain reaction results under different conditions. The composition of gases after reaction was analyzed by a gas phase chromatograph with FID as a detector, with the CO content being rounded to 1 ppm.

By using the above evaluation method, the catalysts of Examples 4 to 5 and Comparative Example 1 were evaluated, and the evaluation results are given in Table 1 below. A smaller CO content at outlet (ppm) indicates a higher catalyst activity.

TABLE 1

Evaluation results of catalyst in CO methanation reaction

| No. | Loading amount of active Ni wt % | Reaction temperature (° C.) | Flow rate of crude hydrogen (ml/min) | Outlet CO (ppm) |
|---|---|---|---|---|
| Example 4 catalyst | 40 | 170 | 800 | <1 |
|  |  |  | 600 | <1 |
|  |  |  | 400 | <1 |
| Example 5 catalyst | 40 | 170 | 800 | <1 |
|  |  |  | 600 | <1 |
|  |  |  | 400 | <1 |
| Comparative Example 1 catalyst | 40 | 170 | 800 | 674 |
|  |  |  | 600 | 34 |
|  |  |  | 400 | <1 |

It can be seen from the results in Table 1 that the outlet CO contents in the inventive examples are much lower than that in the Comparative Example, indicating that the catalysts of the invention have higher activities in low-temperature methanation.

Example 8

Performance test in aldehyde hydrogenation reaction:

The performance of catalysts in reaction was evaluated by using fixed bed n-butyraldehyde liquid-phase hydrogenation test. 20 ml of catalyst were charged into a fixed bed reactor, and n-butyraldehyde liquid-phase hydrogenation test was carried out under conditions of a hydrogen flow rate of 50 ml/min, a reaction temperature of 90 to 130° C., a pressure of 4.0 MPa, and a liquid hourly space velocity of n-butyraldehyde of 0.3 $h^{-1}$. Reaction product was quantified by a gas phase chromatograph with FID as a detector.

TABLE 2

Catalyst activities for the aldehyde hydrogenation

| Catalyst | | n-butyraldehyde conversion (wt % content) | | | |
|---|---|---|---|---|---|
| No. | Loading amount of active Ni wt % | Reaction temperature 90° C. | Reaction temperature 100° C. | Reaction temperature 110° C. | Reaction temperature 130° C. |
| Example 3 catalyst | 45 | 99.99 | 99.99 | 99.99 | 99.99 |
| Example 6 catalyst | 45 | 99.99 | 99.99 | 99.99 | 99.99 |
| Comparative Example 2 catalyst | 45 | 90.50 | 93.50 | 95.50 | 98.90 |
| Comparative Example 3 catalyst | 50 | 99.07 | 99.53 | 99.90 | 99.98 |
| Comparative Example 4 catalyst | 45 | <1 | <1 | <1 | <1 |

TABLE 3

Amount of ether byproduct formed in the aldehyde hydrogenation

| Catalyst | | Amount of n-butyl ether as byproduct (wt % content) | | | |
|---|---|---|---|---|---|
| No. | Loading amount of active Ni wt % | Reaction temperature 90° C. | Reaction temperature 100° C. | Reaction temperature 110° C. | Reaction temperature 130° C. |
| Example 3 catalyst | 45 | 0.073 | 0.178 | 0.266 | 0.710 |
| Example 6 catalyst | 45 | 0.053 | 0.089 | 0.102 | 0.415 |
| Comparative Example 2 catalyst | 45 | 0.159 | 0.292 | 0.677 | 1.70 |
| Comparative Example 3 catalyst | 50 | 0.243 | 0.425 | 0.647 | 1.126 |
| Comparative Example 4 catalyst | 45 | Not detectable | Not detectable | Not detectable | Not detectable |

The conversion results in the aldehyde hydrogenation reaction are shown in Table 2, reflecting how the catalyst activity is. A higher conversion indicates a higher catalyst activity. The results regarding the formation of n-butyl ether byproduct in the aldehyde hydrogenation reaction are shown in Table 3, reflecting how the catalyst selectivity is. A less amount of the formed ether indicates a better selectivity of the catalytic reaction.

It can be seen from the evaluation results in Table 2 and Table 3 that the present catalysts are significantly superior to the catalysts of Comparative Examples in both activity and selectivity, and this means a great application value in industrial production. Comparative Example 3 is a fixed bed Raney nickel catalyst containing alumina, which has an activity in the aldehyde hydrogenation significantly lower than that of the present catalyst, and results in the formation of relatively more n-butyl ether byproduct, indicating that it is markedly inferior to the present catalyst in selectivity. Comparative Example 4 has almost no activity. Maybe the reason is that the metal component is wrapped or covered almost completely by the polymer so that the number of the catalytically active sites is very small. Since the conversion for Comparative Example 4 is very low, the n-butyl ether byproduct is not detectable.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. The present invention has been described above with reference to many embodiments and specific examples. Considering the above detailed description, many variations will be apparent for those skilled in the art. All of such variations will be within the scope of the whole purpose of the appended claims.

In this disclosure, whenever a composition, an element or a group of elements is preceded with the transitional phrase "comprising", it is understood that we also contemplate the same composition, element or group of elements with transitional phrases "consisting essentially of", "consisting of", "selected from the group consisting of", or "is" preceding the recitation of the composition, element, or elements, and vice versa.

What is claimed is:

1. A solid composite catalyst comprising carbon as a continuous phase and Raney alloy particles as a dispersed phase, and at least one promoter selected from the group consisting of Mo, Cr, Ti, Pt, Pd, Rh and Ru,
   wherein the Raney alloy particles comprise at least one first metal selected from the group consisting of nickel, cobalt, copper and iron, and at least one leachable element selected from the group consisting of aluminum, zinc and silicon,
   wherein the Raney alloy particles are dispersed in the continuous phase, and wherein the continuous phase is obtained by carbonizing at least one carbonizable organic matter being an organic polymer, and
   wherein the solid composite catalyst comprises the Raney alloy particles at an amount of from 10 wt. % to 90 wt. %, based on the total weight of the composite catalyst, the at least one promoter accounts for 0.01 wt % to 5 wt % of the total weight of the Raney alloy particles, and the balance amount of the carbon as the continuous phase.

2. The solid composite catalyst of claim 1, characterized at least in one of:
   that the Raney alloy particles have an average particle size of from 0.1 micron to 1000 microns;
   that the carbonizable organic matter is an organic polymer;
   that the solid composite catalyst is in the form of sphere, semi-sphere, ring, semi-ring, trilobal extrudate, cylinder, semi-cylinder, hollow cylinder, prism, cube, cuboid, tablet, pellet, tooth, or irregular particles; and
   that the solid composite catalyst is in the form of particle, and has an average equivalent diameter in a range of from 0.3 mm to 20 mm.

3. The solid composite catalyst of claim 1, wherein in the Raney alloy particles, a weight ratio of the at least one first metal to the at least one leachable element ranges from 1:99 to 10:1.

4. The solid composite catalyst of claim 1, wherein the carbonizable organic matter is a synthetic polymer selected from the group consisting of rubber, thermosetting plastics, and thermoplastic plastics.

5. The solid composite catalyst of claim 4, wherein the carbonizable organic matter is at least one thermosetting plastic selected from the group consisting of epoxy resin, phenolic resin and furan resin.

6. The solid composite catalyst of claim 4, wherein the carbonizable organic matter is at least one thermoplastic plastic selected from the group consisting of polystyrene, poly(styrene-co-divinylbenzene) and polyacrylonitrile.

7. The solid composite catalyst of claim 4, wherein the carbonizable organic matter is at least one rubber selected from the group consisting of butadiene-styrene rubber and polyurethane rubber.

8. The solid composite catalyst of claim 1, wherein the carbonizable organic matter is at least one natural organic polymer selected from the group consisting of starch, modified starch, viscose fiber, lignin, cellulose and carboxymethylcellulose.

9. The solid composite catalyst of claim 1, wherein the carbonizable organic matter is selected from the group consisting of coal, natural bitumen, asphalt, coal-tar pitch and a mixture thereof.

10. The solid composite catalyst of claim 1, characterized in at least one of:
  that the Raney alloy particles have an average particle size of from 1 micron to 500 microns;
  that the solid composite catalyst is in the form of sphere, ring, trilobal extrudate, cylinder, prism, cuboid, tooth, or irregular particles;
  that the solid composite catalyst has a content of the Raney alloy particles from 40 wt. % to 80 wt %, based on the total weight of the solid composite catalyst; and
  that the solid composite catalyst is in the form of particle, and has an average equivalent diameter in a range of from 0.5 mm to 10 mm.

11. The solid composite catalyst of claim 1, wherein in the Raney alloy particles, a weight ratio of the at least one metal selected from the group consisting of nickel, cobalt, copper and iron to the at least one leachable element selected from the group consisting of aluminum, zinc and silicon ranges from 1:10 to 4:1.

12. A solid composite catalyst consisting essentially of carbon as a continuous phase and Raney alloy particles as a dispersed phase,
  wherein the Raney alloy particles comprise at least one first metal selected from the group consisting of nickel, cobalt, copper and iron, and at least one leachable element selected from the group consisting of aluminum, zinc and silicon,
  wherein the Raney alloy particles are dispersed in the continuous phase, and wherein the continuous phase is obtained by carbonizing at least one carbonizable organic matter being an organic polymer, and
  wherein the solid composite catalyst comprises the Raney alloy particles at an amount of from 10 wt. % to 90 wt. %, based on the total weight of the solid composite catalyst, and the balance amount of the carbon as the continuous phase.

13. A method for activating the solid composite catalyst of claim 1, wherein the method comprises treating the solid composite catalyst with a caustic aqueous solution.

14. The method of claim 13, wherein the treating is performed as follows: the solid composite catalyst is treated with a caustic aqueous solution having a concentration of from 0.5 to 50 wt % at 25° C. to 95° C. for 5 minutes to 72 hours.

15. A method for preparing the solid composite catalyst of claim 1, comprising the steps of:
  a) formulating a solidifiable composition, wherein the solidifiable composition or a solidified product thereof comprises a carbonizable organic matter;
  b) mixing the Raney alloy particles with the solidifiable composition from step a), then solidifying the resultant mixture, and optionally crushing the solidified mixture, to obtain a catalyst precursor; and
  c) under inert atmosphere, high-temperature carbonizing the catalyst precursor from step b), to afford the solid composite catalyst.

16. The method of claim 15, characterized at least in one of:
  that the Raney alloy particles have an average particle size of from 0.1 micron to 1000 microns;
  that the carbonizable organic matter is an organic polymer;
  that in step c), the carbonizing temperature ranges from 400° C. to 1900° C., and carbonizing time ranges from 1 hour to 24 hours;
  that in step c), the inert gas is nitrogen or argon; and
  that in step b), a weight ratio of the Raney alloy particles to the solidifiable composition from step a) ranges from 1:99 to 99:1.

17. The method of claim 15, wherein in step b), a weight ratio of the Raney alloy particles to the solidifiable composition from step a) ranges from 10:90 to 90:10.

18. The method of claim 15, wherein in step b), a weight ratio of the Raney alloy particles to the solidifiable composition from step a) ranges from 25:75 to 75:25.

* * * * *